United States Patent
King et al.

(10) Patent No.: US 10,674,968 B2
(45) Date of Patent: Jun. 9, 2020

(54) ADJUSTABLE OVERLAY PATTERNS FOR MEDICAL DISPLAY

(71) Applicant: Karl Storz Imaging, Inc., Goleta, CA (US)

(72) Inventors: Timothy King, Goleta, CA (US); Thomas Prescher, Agoura Hills, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1192 days.

(21) Appl. No.: 13/871,672

(22) Filed: Apr. 26, 2013

(65) Prior Publication Data

US 2013/0245460 A1 Sep. 19, 2013

Related U.S. Application Data

(63) Continuation-in-part of application No. 13/289,554, filed on Nov. 4, 2011.

(60) Provisional application No. 61/441,473, filed on Feb. 10, 2011.

(51) Int. Cl.
*A61B 5/00* (2006.01)
*A61B 1/00* (2006.01)

(52) U.S. Cl.
CPC ............ *A61B 5/743* (2013.01); *A61B 5/0059* (2013.01); *A61B 5/0077* (2013.01); *A61B 5/72* (2013.01); *A61B 5/748* (2013.01); *A61B 1/0005* (2013.01); *A61B 5/749* (2013.01)

(58) Field of Classification Search
CPC ... A61B 1/0005; A61B 5/0059; A61B 5/0077; A61B 5/72; A61B 5/743; A61B 5/748; A61B 5/749
See application file for complete search history.

(56) References Cited

U.S. PATENT DOCUMENTS

| | | | | |
|---|---|---|---|---|
| 4,216,589 A | * | 8/1980 | Beaver | 33/266 |
| 4,559,705 A | * | 12/1985 | Hodge et al. | 33/1 B |
| 5,174,037 A | * | 12/1992 | Curtin | 33/512 |

(Continued)

FOREIGN PATENT DOCUMENTS

| | | |
|---|---|---|
| EP | 2486847 A1 | 8/2012 |
| JP | H07184863 A | 7/1995 |
| WO | 2010088515 A1 | 8/2010 |

OTHER PUBLICATIONS

European Search Report Application No. EP 14 18 8189 Completed: Mar. 19, 2015; dated Mar. 27, 2015 6 pages.

(Continued)

*Primary Examiner* — Michael T Rozanski
(74) *Attorney, Agent, or Firm* — Whitmyer IP Group LLC

(57) ABSTRACT

A system for identifying an area of interest on a surgical image, including a source of surgical image data, which may be a camera, an image processing unit, which may be a camera control unit, and a destination, which may be a display. The image processing unit is configured to receive the surgical image data and combine it with an overlay pattern for identifying an area of interest, which is then displayed on the display. The overlay pattern may include centric lines, concentric ovals, concentric circles, or other concentric shapes. The overlay may include a key with coordinates or labels. Properties of the overlay and the key may be customized and adjusted.

16 Claims, 17 Drawing Sheets

(56) References Cited

U.S. PATENT DOCUMENTS

| | | | |
|---|---|---|---|
| 5,291,560 A * | 3/1994 | Daugman | 382/117 |
| 5,517,278 A * | 5/1996 | Takahara et al. | 396/374 |
| 5,573,492 A * | 11/1996 | Dianna et al. | 600/117 |
| 5,627,915 A * | 5/1997 | Rosser et al. | 382/219 |
| 5,862,517 A * | 1/1999 | Honey et al. | 702/85 |
| 5,892,554 A * | 4/1999 | DiCicco et al. | 348/584 |
| 5,912,700 A * | 6/1999 | Honey et al. | 348/157 |
| 5,917,553 A * | 6/1999 | Honey et al. | 348/578 |
| 5,953,076 A * | 9/1999 | Astle et al. | 348/584 |
| 6,014,472 A * | 1/2000 | Minami et al. | 382/285 |
| 6,037,936 A * | 3/2000 | Ellenby et al. | 715/764 |
| 6,057,833 A * | 5/2000 | Heidmann et al. | 715/726 |
| 6,100,925 A * | 8/2000 | Rosser et al. | 348/169 |
| 6,134,346 A * | 10/2000 | Berman et al. | 382/163 |
| 6,359,644 B1 | 3/2002 | Salvati | |
| 6,414,696 B1 * | 7/2002 | Ellenby et al. | 715/762 |
| 6,431,768 B1 * | 8/2002 | Nakamura | 396/348 |
| 6,535,756 B1 * | 3/2003 | Simon et al. | 600/424 |
| 6,630,937 B2 | 10/2003 | Kallergi et al. | |
| 6,725,080 B2 * | 4/2004 | Melkent et al. | 600/424 |
| 7,033,172 B2 * | 4/2006 | Hansen et al. | 433/29 |
| 7,075,556 B1 * | 7/2006 | Meier et al. | 345/629 |
| 7,366,934 B1 | 4/2008 | Narayan et al. | |
| 7,427,263 B2 | 9/2008 | Hoeg et al. | |
| 7,492,363 B2 * | 2/2009 | Meier et al. | 345/419 |
| 7,590,335 B2 * | 9/2009 | Kobayashi et al. | 396/50 |
| 7,607,079 B2 | 10/2009 | Reiner | |
| 7,782,384 B2 * | 8/2010 | Kelly | 348/333.01 |
| 7,811,224 B2 | 10/2010 | Hale et al. | |
| 7,812,851 B2 * | 10/2010 | Inakura | 345/629 |
| 7,864,996 B2 * | 1/2011 | Hemmer et al. | 382/128 |
| 7,907,166 B2 * | 3/2011 | Lamprecht et al. | 348/43 |
| 7,949,965 B2 * | 5/2011 | Tominaga | 715/764 |
| 8,073,528 B2 * | 12/2011 | Zhao et al. | 600/424 |
| 8,213,788 B2 * | 7/2012 | Soli et al. | 396/373 |
| 8,600,133 B2 * | 12/2013 | Buelow et al. | 382/128 |
| 8,830,224 B2 * | 9/2014 | Zhao et al. | 345/419 |
| 2002/0049375 A1 | 4/2002 | Strommer et al. | |
| 2003/0069975 A1 | 4/2003 | Abjanic et al. | 709/227 |
| 2003/0091218 A1 * | 5/2003 | Hamid | 382/124 |
| 2003/0114730 A1 | 6/2003 | Hale et al. | |
| 2004/0085455 A1 * | 5/2004 | Silverstein | 348/211.4 |
| 2005/0065435 A1 * | 3/2005 | Rauch et al. | 600/427 |
| 2005/0075535 A1 | 4/2005 | Shapiro et al. | |
| 2005/0093889 A1 | 5/2005 | Sauer et al. | |
| 2005/0146622 A9 * | 7/2005 | Silverstein | 348/211.4 |
| 2005/0177026 A1 * | 8/2005 | Hoeg | A61B 1/0051 600/173 |
| 2006/0098112 A1 * | 5/2006 | Kelly | 348/333.12 |
| 2006/0152516 A1 * | 7/2006 | Plummer | 345/538 |
| 2006/0217689 A1 * | 9/2006 | Dick et al. | 606/4 |
| 2006/0257008 A1 | 11/2006 | Nolle et al. | |
| 2006/0258938 A1 * | 11/2006 | Hoffman et al. | 600/424 |
| 2006/0259193 A1 * | 11/2006 | Wang et al. | 700/245 |
| 2006/0291702 A1 * | 12/2006 | Miessbacher | 382/117 |
| 2007/0073161 A1 * | 3/2007 | Davidson | 600/476 |
| 2007/0106282 A1 * | 5/2007 | Lavallee | 606/1 |
| 2007/0147707 A1 | 6/2007 | Coste-Maniere et al. | |
| 2007/0156017 A1 * | 7/2007 | Lamprecht et al. | 600/102 |
| 2007/0269092 A1 * | 11/2007 | Hill et al. | 382/131 |
| 2008/0004603 A1 * | 1/2008 | Larkin et al. | 606/1 |
| 2008/0015415 A1 | 1/2008 | Obata et al. | |
| 2008/0071142 A1 | 3/2008 | Gattani et al. | |
| 2008/0192116 A1 * | 8/2008 | Tamir et al. | 348/157 |
| 2008/0303899 A1 | 12/2008 | Berci | |
| 2009/0036902 A1 | 2/2009 | DiMaio et al. | |
| 2009/0087067 A1 * | 4/2009 | Khorasani | 382/132 |
| 2009/0088634 A1 * | 4/2009 | Zhao et al. | 600/427 |
| 2009/0088897 A1 * | 4/2009 | Zhao et al. | 700/250 |
| 2009/0146950 A1 | 6/2009 | Maringelli | |
| 2009/0156895 A1 * | 6/2009 | Higgins et al. | 600/104 |
| 2009/0171184 A1 | 7/2009 | Jenkins et al. | |
| 2009/0190808 A1 | 7/2009 | Claus | |
| 2009/0235570 A1 | 9/2009 | Sammut et al. | |
| 2009/0248041 A1 * | 10/2009 | Williams et al. | 606/130 |
| 2009/0271738 A1 | 10/2009 | Glaser-Seidnitzer et al. | |
| 2009/0276725 A1 | 11/2009 | Glaser-Seidnitzer et al. | |
| 2010/0094085 A1 * | 4/2010 | Yamamoto et al. | 600/109 |
| 2010/0160789 A1 * | 6/2010 | Dilworth et al. | 600/476 |
| 2010/0166323 A1 * | 7/2010 | Zhao et al. | 382/218 |
| 2010/0168765 A1 * | 7/2010 | Moraviec | 606/130 |
| 2010/0208951 A1 * | 8/2010 | Williams et al. | 382/117 |
| 2010/0228249 A1 * | 9/2010 | Mohr et al. | 606/41 |
| 2011/0135149 A1 * | 6/2011 | Gefen | 382/103 |
| 2011/0137156 A1 * | 6/2011 | Razzaque et al. | 600/424 |
| 2011/0170755 A1 * | 7/2011 | Buelow et al. | 382/128 |
| 2011/0235891 A1 * | 9/2011 | Sonnemans et al. | 382/133 |
| 2012/0038744 A1 * | 2/2012 | Naka | H04N 13/0454 348/43 |
| 2012/0158019 A1 * | 6/2012 | Tenney et al. | 606/133 |
| 2012/0209123 A1 * | 8/2012 | King | A61B 1/00 600/476 |
| 2013/0197357 A1 * | 8/2013 | Green et al. | 600/424 |
| 2014/0037165 A1 * | 2/2014 | King | A61B 5/748 382/128 |
| 2014/0051986 A1 * | 2/2014 | Zhao et al. | 600/424 |
| 2014/0055489 A1 * | 2/2014 | Itkowitz et al. | 345/633 |
| 2014/0111623 A1 * | 4/2014 | Zhao et al. | 348/47 |
| 2014/0142422 A1 * | 5/2014 | Manzke et al. | 600/424 |
| 2014/0176661 A1 * | 6/2014 | Smurro et al. | 348/14.06 |
| 2014/0267603 A1 * | 9/2014 | Kerdok et al. | 348/43 |
| 2014/0275760 A1 * | 9/2014 | Lee et al. | 600/102 |

OTHER PUBLICATIONS

European Search Report Application No. EP 12 15 4966 Completed: May 31, 2012; dated Jun. 12, 2012 6 pages.

European Search Report Application No. EP14166034 Completed: Aug. 25, 2014; dated Sep. 1, 2014 pp. 6.

Yang et al., "Informatics in Radiology (infoRAD) Multimedia Extension of Medical Imaging Resource Center Teaching Files", RadioGraphics 2005; 25:1699-1708.

Adler et al., "Overlay of Patient-Specific Anatomical Data for Advanced Navigation in Surgery Simulation", IWDE 2010 Magdeburg, Germany.

European Office Action Application No. 14188189.6 Completed: Dec. 17, 2015 4 Pages.

Canadian Office Action Application No. 2,766,595 dated Apr. 27, 2016 5 Pages.

European Office Action Application No. 12154966.1 dated Mar. 22, 2016 4 Pages.

* cited by examiner

ADJUSTABLE OVERLAY PATTERNS FOR MEDICAL DISPLAY

This patent application claims the benefit, under 35 U.S.C. § 120, of U.S. patent application Ser. No. 13/289,554, filed on Nov. 4, 2011, which claims the benefit, under 35 U.S.C. § 119(e), of U.S. Provisional Patent Application Ser. No. 61/441,473, filed on Feb. 10, 2011, the content of both of which are incorporated herein by reference in their entirety.

FIELD OF THE INVENTION

The present invention relates to a system for displaying images from a surgical procedure. Specifically, the present invention relates to a method and apparatus for generating an overlay aid on images from a live surgical procedure.

BACKGROUND OF THE INVENTION

In modern medicine, treatments are being carried out more and more using technical imaging methods. By way of example, miniaturized cameras are inserted into the body of a patient, and the image taken by the camera is displayed to the physician on a monitor installed in his/her working area. In this way, the physician can, for example, examine an internal organ or a joint for diagnostic purposes and he/she can also carry out surgical operations in a minimally invasive fashion. By arranging a monitor in the working area of the physician, i.e. in the sterile area, the physician may track all the operations that he or she undertakes on the patient live on the monitor, the corresponding monitor image being picked up by the medical imaging system. Accordingly, during various types of minimally invasive surgeries, such as, endoscopic, arthroscopic and laparoscopic procedures, a surgeon is able to visibly examine the interior of an organ, joint or other anatomical structure while the surgeon is conducting the surgery.

Recent developments have resulted in systems incorporating various audiovisual devices to allow others in the surgical suite or located remotely therefrom who may be assisting or observing, to better monitor the surgical procedure. Accordingly, both still images and live video being acquired during the surgery can be output to various different monitors or recording devices both within, and outside of the surgical suite. Additionally, various devices have been incorporated into these systems to allow the surgeon, or other individuals assisting or observing, to utilize the imaging capabilities of the system in different ways, simultaneously or at different times, for a variety of different objectives.

Moreover, when there are multiple persons assisting in or observing a surgery, it is often necessary to call attention to or identify certain areas of interest within the patient's body shown on a live surgical monitor. For example, an instructor may wish to call attention to certain internal organs or structures, pathologies or procedures to students while observing a surgery. In addition, a supervising surgeon may direct the main practitioner to add more sutures in an area of interest.

In order to further improve communication during these surgical procedures, it is desired to have a method or device for calling attention to or identifying certain areas of interest displayed on the live surgical monitor. This would facilitate efficient and clear communication regarding a particular area of interest and diminish confusion, misunderstandings and misinterpretations.

Certain methods and devices have been tried to identify regions of interest on a live surgical monitor, including, use of a laser pointer or cursor or "circling" or annotating on a touch screen by the surgeon or assistants, or others assisting in or observing the surgery. These known methods have many disadvantages. First, the surgeon cannot operate a laser pointer or make indications on a touch screen while also safely performing the surgical procedure. Second, these known methods, including the use of a cursor, require the use of an additional hand, which the surgeon often cannot spare.

SUMMARY OF THE INVENTION

Against this background, it is an object of the present invention to provide a method and an apparatus for identifying regions of interest on images displayed on a live surgical monitor.

It is another object of the invention to provide such a method and apparatus in a simple and cost effective way.

It is another object of the invention that the image properties of the method and/or apparatus for identifying regions of interest be configurable and adjustable.

It is yet another object of the invention to enable a physician to configure and adjust the properties of the image in and around an identified region of interest.

In accordance with one aspect of the invention, a configurable overlay pattern for identifying regions of interest on a surgical monitor. In another aspect, the areas of interest defined by the overlay pattern may be labelled with coordinates, such as numbers and/or letters, for ease of reference. If, for example, the overlay pattern is a grid, the rows and columns of the grid may be labelled with Cartesian coordinates. In accordance with another aspect of the invention, the properties of the surgical image in and/or around an identified region of interest may be adjusted. In accordance with a further aspect of the invention, the overlay pattern may be applied to displayed images recalled from an image archive. The applied overlay pattern may also be maintained on captured images that are subsequently saved to an archive.

Moreover, the novel method and apparatus have the advantage that the surgical image including the overlay pattern is directly available for further processing outside the sterile area. This further processing can include, for example, displaying on a remote training monitor and/or archiving in an electronic patient card file. The novel system therefore offers an extended field of application.

In one aspect, a system for identifying an area of interest on a surgical image, comprising a camera for generating surgical image data; a camera control unit receiving and processing said surgical image data from said camera; software executing on said camera control unit for applying an overlay pattern to said surgical image data; and a display controlled by said camera control unit for displaying said surgical image data and said overlay pattern, is provided. The system may also include a storage device for saving the surgical image data and the overlay pattern. The surgical image data may be video data, still frame data or combinations thereof. The overlay pattern itself may comprise a grid, crosshairs, quadrants, one or more hash marks, a circle or an oval and the pattern may be applied centered on the image as displayed or at the edges. A key for identifying one or more regions of the overlay pattern may also be provided. At least one property of the overlay pattern may also be adjustable, including brightness, contrast, opacity, resolution and color. The properties of the overlay may be adjusted via one or more buttons located on said camera, via a touchscreen or via voice recognition software executing on the camera control unit.

In another aspect, a system for identifying an area of interest on a surgical image, comprising a source of surgical image data; an image processing unit in communication with said source, the surgical image processing unit being configured to receive the surgical image data and combine it with an overlay pattern for identifying an area of interest; and a destination in communication with said image processing unit for receiving said surgical image data combined with said overlay pattern, is provided. The system may further include software executing on said image processing unit for combining said surgical image data with said overlay pattern. The source of image data, which may be video data, still frame data and combinations thereof, may be a camera, a storage medium, or a camera control unit. The destination may be a display, which may be configured to simultaneously display surgical image data from more than one source in combination with an overlay pattern, or a storage medium.

In yet another aspect, a method for identifying an area of interest on a surgical image, comprising providing a source of surgical image data; transmitting the surgical image data to a camera control unit from the source; combining said surgical image data with an overlay pattern in said camera control unit; transmitting said surgical image data combined with said overlay pattern to a display; displaying said surgical image data combined with said overlay pattern on said display, is provided. Software executing on said camera control unit for combining said surgical image data with said overlay pattern may also be provided. The method may also include the step of saving the surgical image data combined with said overlay pattern to a storage medium in communication with said camera control unit. The method may further comprise the steps of selecting a desired pattern, adjusting the source of image data such that an area of interest is located near a region of said overlay pattern, and identifying an area of interest in said surgical image data by referencing said overlay pattern.

In a further aspect, the overly pattern for the display may comprise centric lines, concentric shapes, or a combination thereof. Preferably, the concentric shapes are concentric ovals, concentric circles, and concentric polygons. In some embodiments, the diameters of the concentric circles are at 25% and 50% of the height of said display. In other embodiments, the centric lines originate from a single point and are shown for every 15 degrees, 20 degrees, 30 degrees, 45 degrees, 60 degrees, or 90 degrees.

It goes without saying that the features mentioned above and those yet to be explained below can be used not only in the combination respectively specified, but also in other combinations or on their own without departing from the scope of the present invention.

BRIEF DESCRIPTION OF THE DRAWINGS

FIG. 2 is a view of an embodiment of an input for use with the system for identifying an area of interest on a surgical image as shown in FIG. 1 or 1a.

FIG. 3 is a view of an overlay pattern in the form of a grid with a key, both at 100% opacity, combined with surgical image data, for use with the system for identifying an area of interest on a surgical image as shown in FIG. 1 or 1a.

FIG. 4 is a view of an overlay pattern in the form of a grid with a key, both at 50% opacity, combined with surgical image data, for use with the system for identifying an area of interest on a surgical image as shown in FIG. 1 or 1a.

FIG. 5 is a view of an overlay pattern combined in the form of a grid at 50% opacity and a key at 100% opacity, combined with surgical image data, for use with the system for identifying an area of interest on a surgical image as shown in FIG. 1 or 1a.

FIG. 6 is a view of an overlay pattern in the form of a grid with a key, both at 100% opacity, combined with surgical image data that has been zoomed in, for use with the system for identifying an area of interest on a surgical image as shown in FIG. 1 or 1a.

FIG. 7 is a view of an overlay pattern in the form of a centered crosshairs, combined with surgical image data, for use with the system for identifying an area of interest on a surgical image as shown in FIG. 1 or 1a.

FIG. 8 is a view of an overlay pattern for use with the system for identifying an area of interest on a surgical image as shown in FIG. 1 or 1a.

FIG. 9 is a view of an overlay pattern for use with the system for identifying an area of interest on a surgical image as shown in FIG. 1 or 1a.

FIG. 10 is a view of an overlay pattern for use with the system for identifying an area of interest on a surgical image as shown in FIG. 1 or 1a.

FIG. 11 is a view of an overlay pattern for use with the system for identifying an area of interest on a surgical image as shown in FIG. 1 or 1a.

FIG. 12 is a view of an overlay pattern for use with the system for identifying an area of interest on a surgical image as shown in FIG. 1 or 1a.

FIG. 13 is a view of an overlay pattern for use with the system for identifying an area of interest on a surgical image as shown in FIG. 1 or 1a.

FIG. 14 is a view of an overlay pattern for use with the system for identifying an area of interest on a surgical image as shown in FIG. 1 or 1a.

FIG. 15 is a view of an overlay pattern for use with the system for identifying an area of interest on a surgical image as shown in FIG. 1 or 1a.

FIG. 16 is a view of an overlay pattern for use with the system for identifying an area of interest on a surgical image as shown in FIG. 1 or 1a.

FIG. 17 is a view of an overlay pattern for use with the system for identifying an area of interest on a surgical image as shown in FIG. 1 or 1a.

FIG. 18 is a view of an overlay pattern for use with the system for identifying an area of interest on a surgical image as shown in FIG. 1 or 1a.

FIG. 19 is a view of an overlay pattern for use with the system for identifying an area of interest on a surgical image as shown in FIG. 1 or 1a.

FIG. 20 is a view of an overlay pattern for use with the system for identifying an area of interest on a surgical image as shown in FIG. 1 or 1a.

FIG. 21 is a view of an overlay pattern for use with the system for identifying an area of interest on a surgical image as shown in FIG. 1 or 1a.

FIG. 22 is a view of an overlay pattern for use with the system for identifying an area of interest on a surgical image as shown in FIG. 1 or 1a.

FIG. 23 is a view of an overlay pattern for use with the system for identifying an area of interest on a surgical image as shown in FIG. 1 or 1a.

FIG. 24 is a view of an overlay pattern for use with the system for identifying an area of interest on a surgical image as shown in FIG. 1 or 1a.

FIG. 25 is a view of an overlay pattern for use with the system for identifying an area of interest on a surgical image as shown in FIG. 1 or 1a.

DETAILED DESCRIPTION OF THE INVENTION

The present invention provides a system 10 for identifying certain areas of interest in surgical image data by applying an overlay pattern, such as a Cartesian grid, crosshairs, quadrants, etc., on the surgical image. The overlay pattern allows a surgeon to then refer or call attention to areas of interest in the surgical image data by referencing the overlay pattern or a portion thereof. As will be discussed in detail below, the overlay may also include an key, which may include alphanumeric labels or coordinates, which may assist the surgeon in identifying the area or portion of the overlay to which he/she is referring.

Figure 1:
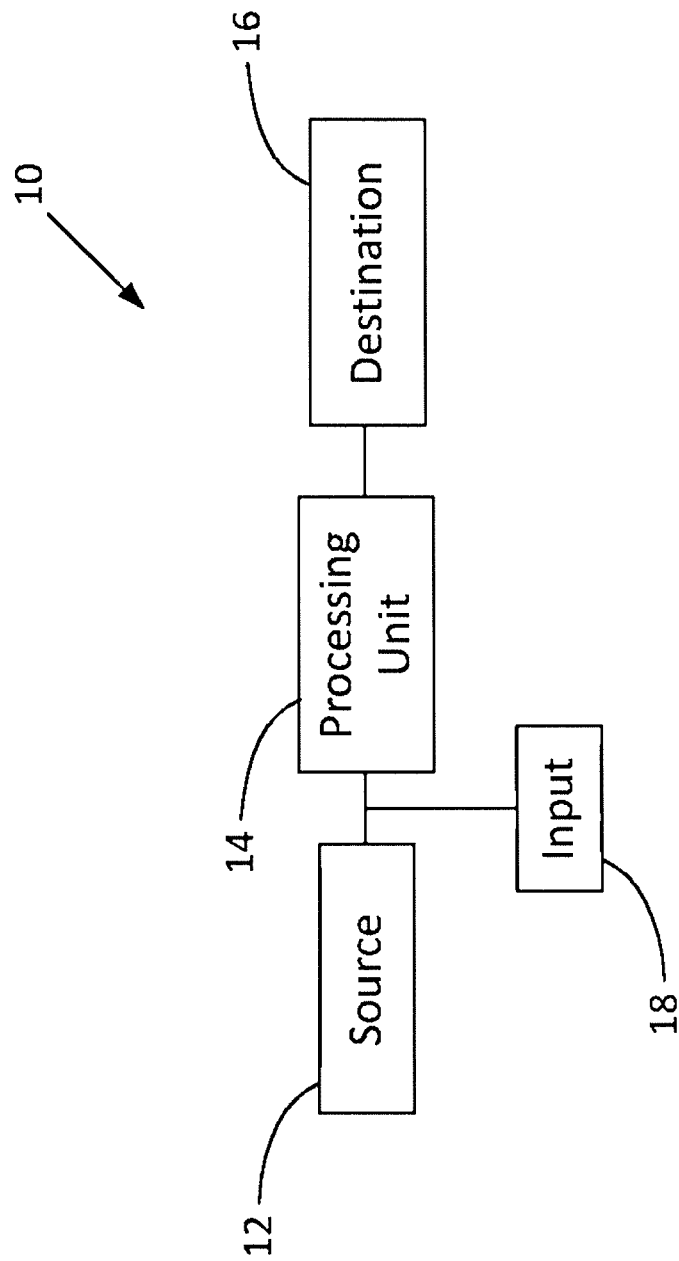
FIG. 1 is a schematic illustration of one embodiment of a system for identifying an area of interest on a surgical image.

Referring to FIG. 1, the system 10 includes at least one source 12 of surgical image data in communication with at least one processing unit 14 and at least one destination 16 for the surgical image data. The at least one source 12 of surgical image data connected to the processing unit 14 may include any device, system, or network that generates, acquires, stores, monitors, or controls surgical image data for use in generating medical images, such as still frame images or video. For example, the at least one source 12 may include an image acquisition device, such as endoscopic cameras, video endoscopes, room cameras, light cameras, and boom cameras. Likewise, the at least one source 12 may include any recording, storage, and/or archival device or system, such as traditional video cassette recorders or digital video recording devices (such as a linear tape deck or DVD recording device), image capture devices, a PACS (Picture Archiving and Communication System) computer, or a Hospital Information System. Finally, the at least one source 12 may include any other device from which surgical image data may be received, such as a patient monitor or a central computer for controlling various devices, or may simply be auxiliary inputs for connecting external devices that may supply surgical image data to the system.

Additionally, a source 12 may be a source of surgical image data that receives surgical image data from yet another source. For example, a source may be a linear tape deck that is recording live video as it supplies the video to the computer. The linear tape deck, in turn, may receive the live video from an endoscopic camera presently being used on a patient, as is further described below. As another example, a source 12 may be a processor for routing images from multiple other sources to the processing unit (i.e., a screen splitter), such as a quad image processor. The source 12 connected to the processing unit may also be a camera control unit (CCU).

The at least one processing unit 14 may include any device, system, or network that processes images generated from surgical image data. For example, the processing unit 14 may be a general processor, a computer, or a CCU, which may be integrated in a camera or may be a modular CCU external to the camera.

The at least one destination 16 for the surgical image data supplied by the at least one source 12 may include any device, system, or network that displays surgical images generated from the image data, or otherwise communicates the image data to viewers, or stores the image data. For example, the at least one destination may include any of various displays, such as, for example, a flat panel display, a plasma screen, or a computer monitor. Additionally, the at least one destination may include a recording device or a storage medium.

Further, the at least one destination 16 for the surgical image data may be located within the operating room, or it may be at a location remote from the operating room. One object of the invention is to assist all those viewing or analyzing surgical image data to identify areas of interest in the surgical image data. For example, an overlay pattern applied to surgical image data may be used by a surgeon performing the surgery to communicate with an assisting surgeon that is not present in the operating room, but who is able to view the surgical image data with the overlay pattern on a destination 16, such as a monitor, at some other remote location. Further, the overlay pattern may be applied to surgical image data displayed on a monitor located in a lecture hall or classroom for teaching purposes.

Moreover, the destination 16 may be capable of displaying surgical image data from more than one source. For example, the destination 16 may be a monitor with picture-in-picture (PIP) capabilities. In this embodiment, the user may choose to apply (or presets may set) an overlay pattern to all or some sets of surgical image data displayed on the monitor. Similarly, if there are several destinations 16 for surgical image data from several sources 12, then user may choose to apply (or presets may set) an overlay pattern to all or some sets of surgical image data sent to the destinations 16.

As illustrated in FIG. 1, the system 10 may also include at least one input 18 in communication with the at least on source 12 and/or the processing unit 14. The at least one input 18 may include any interface whereby a user to enable/disable and/or adjust the properties of the overlay pattern. In one embodiment, the input 18 may be a button or menu located on the source 12 of surgical image data, such as an endoscopic camera, itself. Alternatively, the input 18 may be a user interface that may include physical buttons for a surgeon to press, or may also include a touch-screen monitor.

Figure 2:
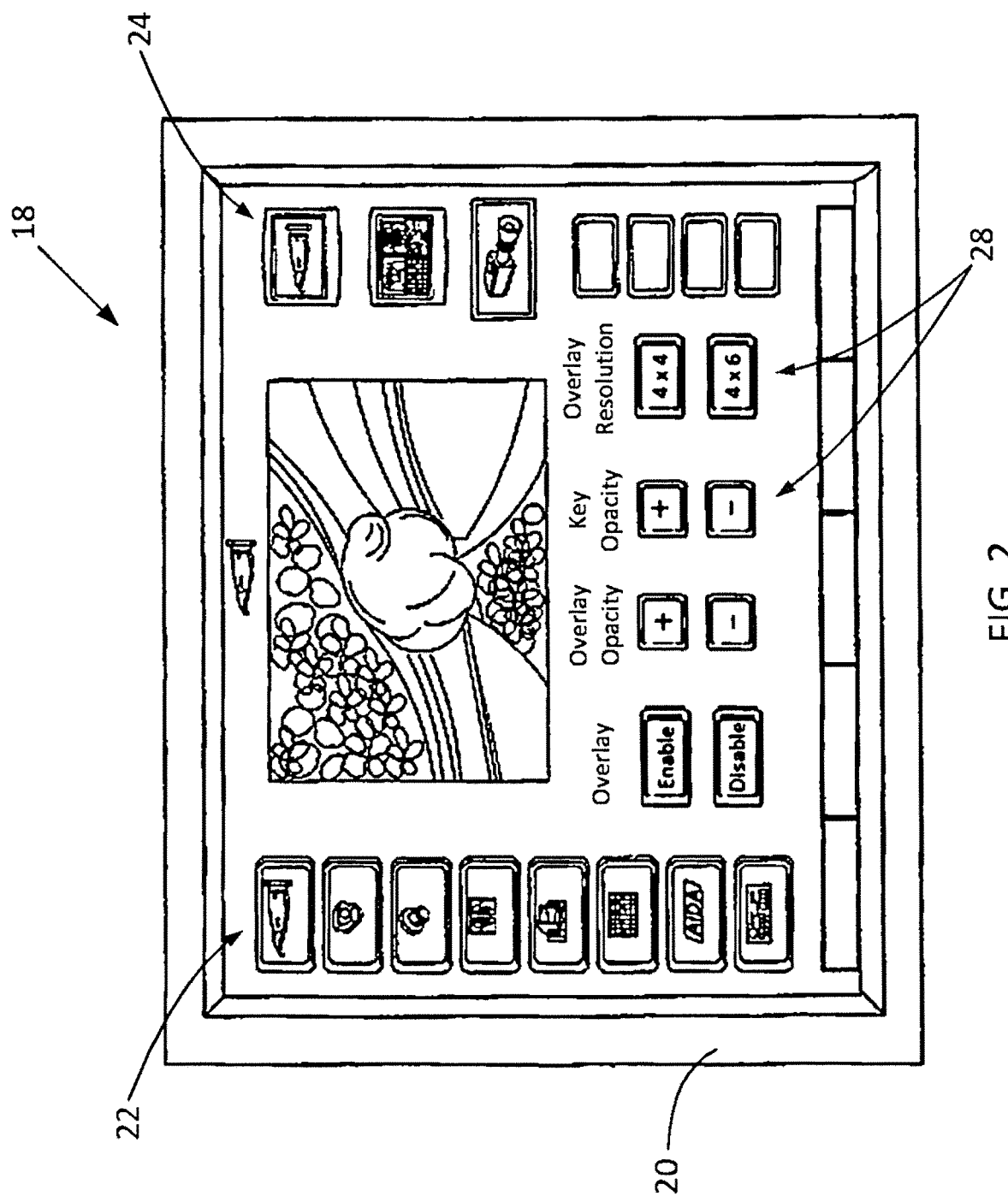

In another embodiment, shown in FIG. 2, the input 18 may include one or more icons on a touchscreen 20. In this embodiment, the system 10 may include software executing on the processing unit 14 that causes the touchscreen 20 to simultaneously display several icons. The icons are sensitive to the touch of the user and will cause a command to be sent to the processing unit 14. By pressing certain source icons 22 or destination icons 24, the user can select a particular source and destination by pressing the touchscreen 20 at the locations of the icon. The user can also manipulate or alter the surgical images being displayed in the display window 26 on the touch screen in order to affect the surgical images ultimately being communicated to the destinations. For example, the touchscreen 20 may also include at least one icon 28 which allows the user to enable/disable the overlay pattern, adjust the properties of the overlay pattern, and select which surgical image data to which the overlay pattern will be applied and to which destination 16 the combined surgical image will be transmitted.

In some embodiments, the system 10 may also be configured to accept voice commands, allowing the user to vocally enable or disable the overlay pattern and adjust properties of the overlay pattern itself without having to touch the imaging device or user interface. In this embodiment, the at least one input 18 may include voice recognition software executing on said processing unit 14 for accepting voice commands, allowing the surgeon to vocally enable or disable the overlay and adjust properties of the overlay itself without having to physically touch the source 12, processing unit 14 or input 18 themselves.

In some further embodiments, the input 18 may include accelerometer data from the camera head or image motion vector detection. The overlay pattern may be automatically enabled or disabled or the properties of the overlay pattern may be adjusted in response to the input of this data.

The input 18 may also include preset data saved by the user that will act on the processing unit 14 to enable/disable the overlay pattern at certain times as preset by the user. The preset data may also include the preferred type of overlay pattern and/or the properties of the overlay pattern the user desires to be sent to the destination 16.

As shown in FIGS. 3 and 7-21, the overlay pattern 30 may be provided in any number of designs, which may be set by the user. For example, as shown in FIGS. 3-6, the overlay pattern 30 may be a grid. In addition, as shown in FIG. 7, the overlay pattern 30 may include a single crosshairs placed at the center of the surgical image as displayed. In other embodiments, the overlay pattern may be one or more hash marks or crosshairs overlaid across a portion of the surgical image, the entire surgical image, or at the edges of the image. The overlay may also be separated into quadrants, with any number of circles, ovals hash marks or any combination thereof within the quadrants. The overlay may also be one or more circles, ovals or other shapes.

The desired overlay pattern 30 may be chosen by the user through an input 18, some examples of which are described above. For example, the source 12, such as an endoscopic camera, may include buttons for selecting and setting a desired overlay pattern 30. The user may also chose to apply the overlay pattern 30 to one or all of the sources 12 of surgical image data 34. Once the overlay pattern 30 is selected, the surgical image data 34 from the one or more selected sources 12 is combined with the overlay pattern 30 in the processing unit 14 and the combined surgical image is transmitted to the one or more selected destinations 18.

Figure 3:
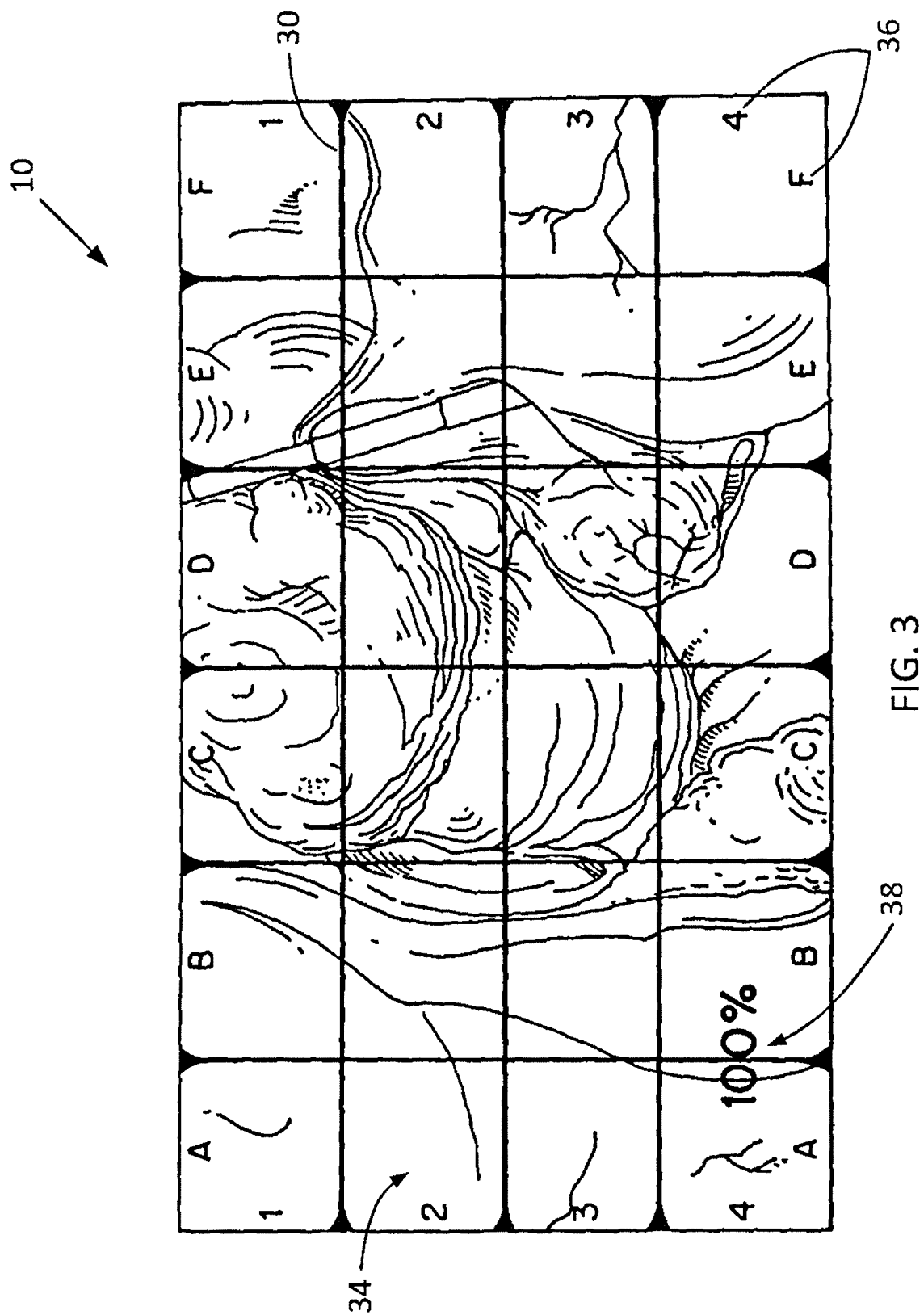

In one embodiment, the overlay pattern is applied to live surgical images, in real time. For example, as shown in FIG. 3, the combined surgical image data 34 and overlay pattern 30 may be transmitted to a display 32. The display may be located in the operating room and/or it may be located somewhere remote from the operating room for viewing by other surgeons assisting in the surgery or by students observing the surgery for educational purposes.

Further, the overlay pattern 30 may be applied to surgical image data 34 that has been recalled from an image archive, such as on a storage medium. The applied overlay pattern 30 may also be maintained on captured surgical image data 34 that is subsequently saved to an archive and may be recalled later for viewing on a display.

The overlay pattern 30 may be applied to the surgical image data at a "fixed" position, meaning that the overlay 30 will be applied at a fixed position with respect to the displayed image, i.e., centered on the surgical image. However, the user may adjust the surgical image data 34 separately with respect to the overlay pattern 30. In operation, the user views the surgical image data with the overlay pattern 30 on a display 32 and adjusts the image captured by the source 12 (i.e., a camera) until the particular area of interest is located at or near an identifiable region of the overlay pattern 30. Using the embodiment shown in FIG. 7, the surgeon will adjust the field of view of the camera until the area of interest is centered at the crosshairs. This allows the surgeon to unequivocally "point" to the area of interest, simply by adjusting the camera.

Figure 11:
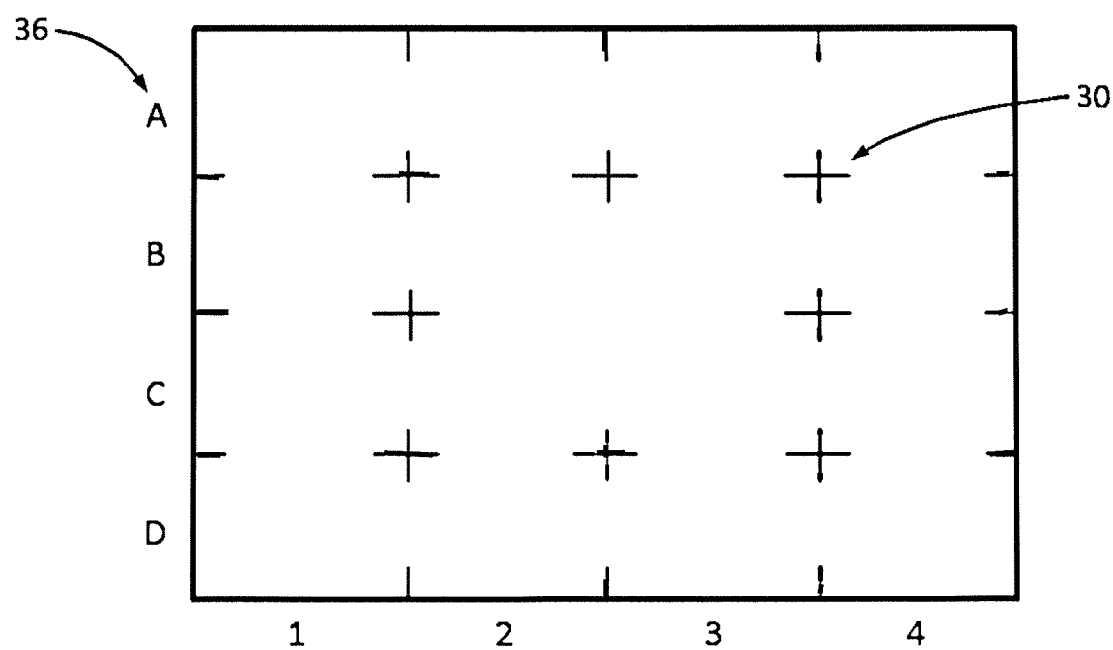
Figure 12:
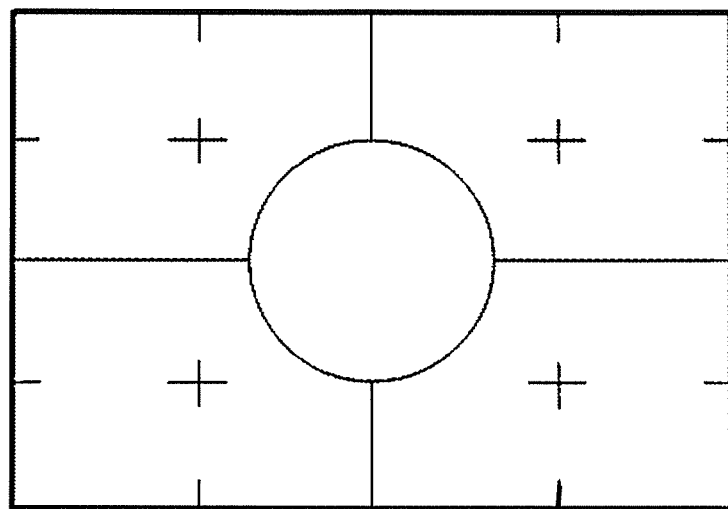
Figure 13:
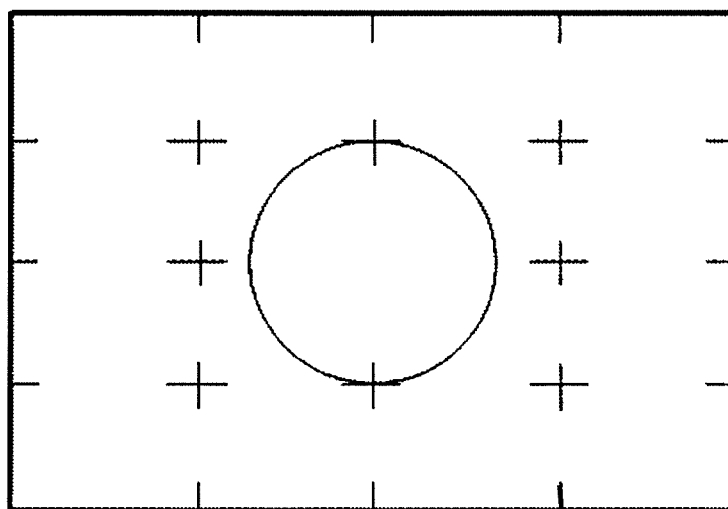
Figure 16:
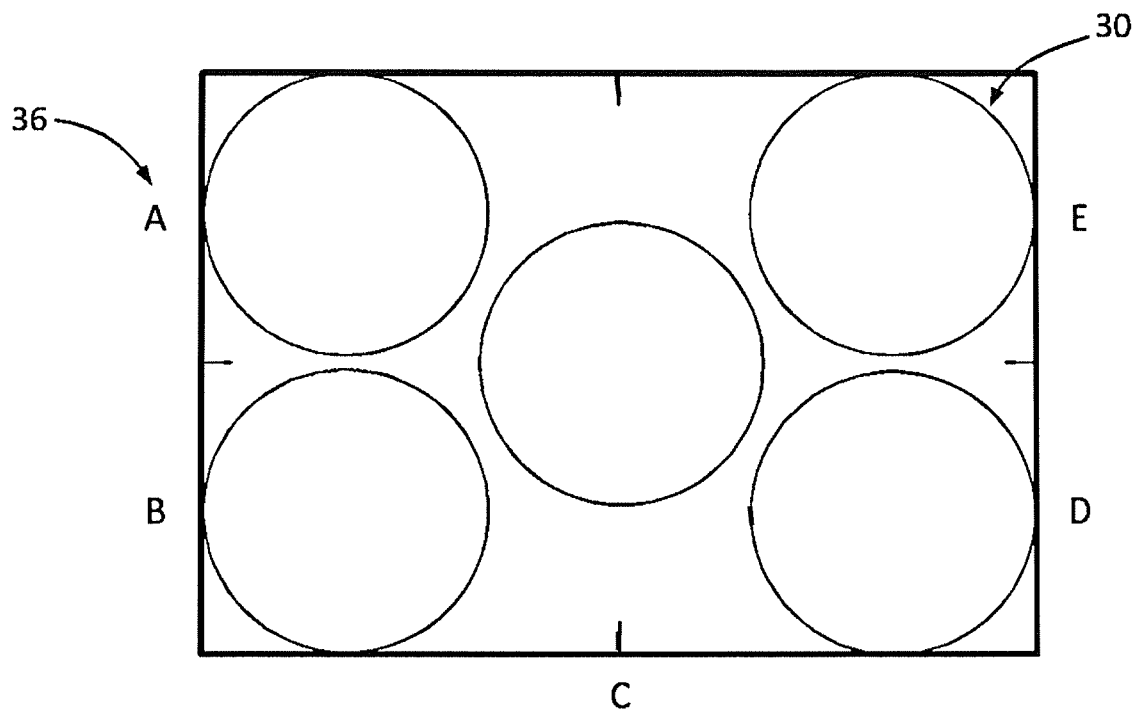
Figure 17:
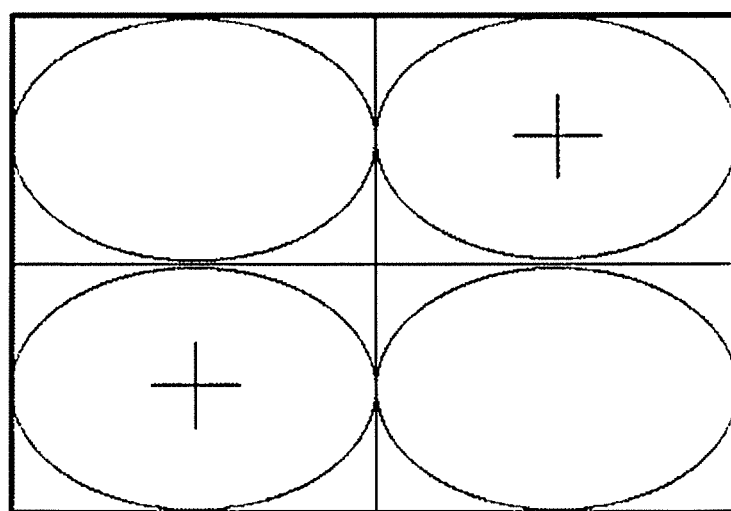
Figure 18:
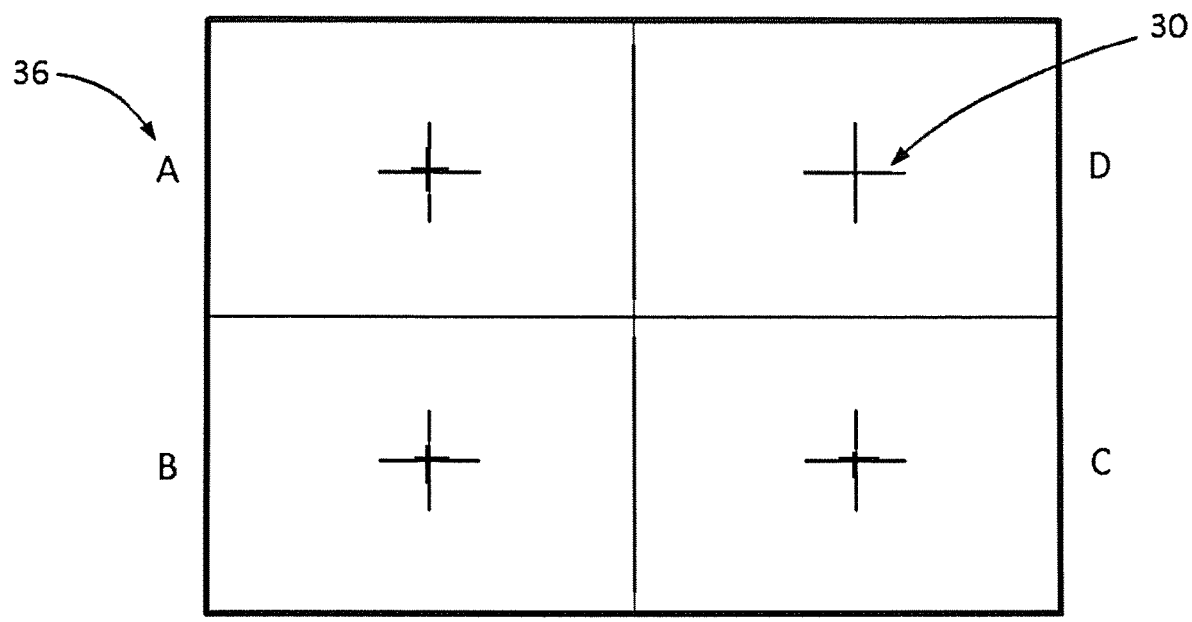
Figure 19:
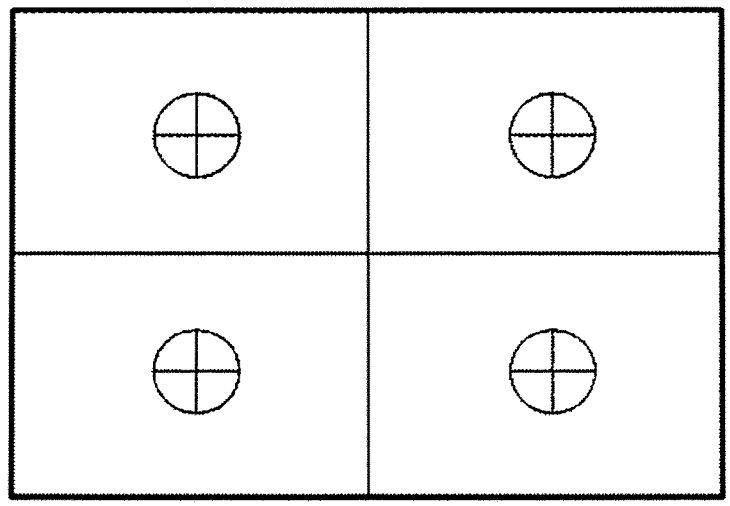
Figure 20:
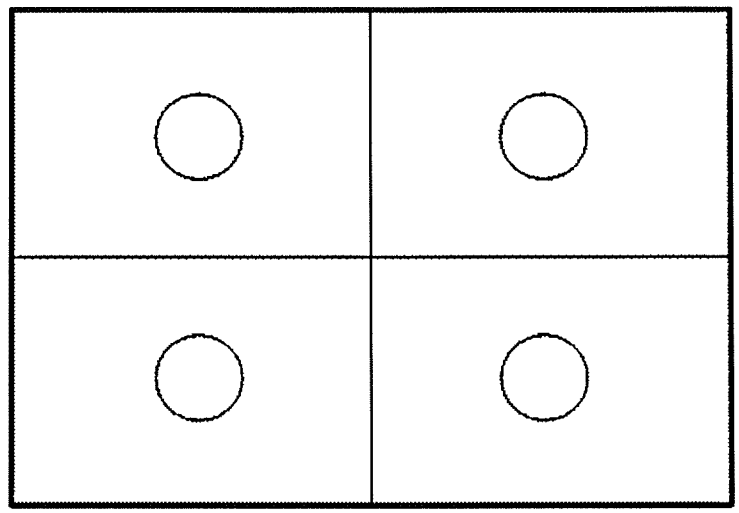
Figure 21:
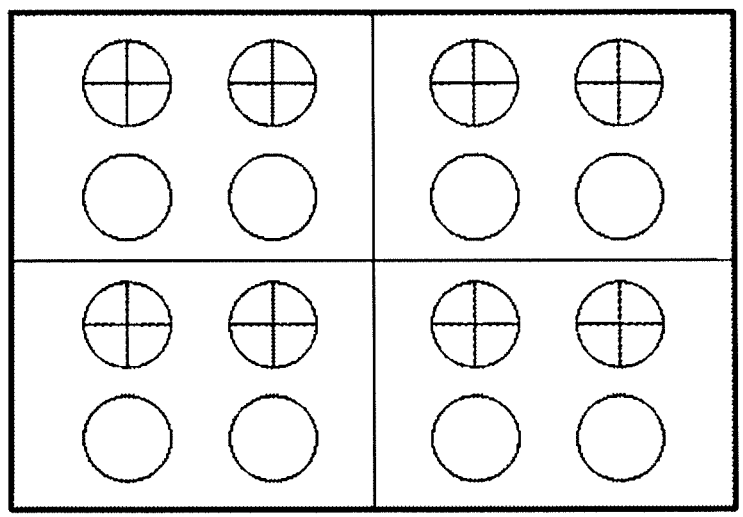

The overlay pattern may also include a key 36 for assisting the user in identifying and discussing areas or portions of the overlay pattern 30, and, in turn, identifying and discussing an area of interest on the underlying surgical image data 34. In one example, the key 36 may include alphanumeric labels or coordinates. For example, as shown in FIG. 3 the rows and columns of a grid overlay may be labeled with letters and numbers—the vertical axis labeled with letters and the horizontal axis labeled with numbers (or vice versa) allowing reference to an area of the surgical image with a simple letter-number combination (e.g. "C3" or "D2", etc.). In another embodiment, if the overlay pattern 30 comprises hash-marks as shown in FIG. 11, the hash marks may be labeled with coordinates. As shown in FIGS. 16 and 18, the quadrants or other defining shapes may be individually labeled with an alphanumeric key 36.

Certain properties of the overlay 30 and key 36 may be adjustable, including, but not limited to, the resolution (i.e., number of rows by number of columns, number of circles, etc.) of the overlay, the opacity of the overlay pattern 30 and/or key 36, the distribution of the opacity of the overlay pattern 30 and/or key 36, the color of the overlay 30 and/or key 36, the brightness of the overlay 30 and/or key 36, the thickness of the lines of the overlay pattern 30, the size of the font of the key 36, etc. The user may choose to enable the overlay pattern and set its properties prior to the start of the surgical procedure, or the overlay may be enabled/disabled and the properties may be adjusted at any time during the surgical procedure.

Figure 4:
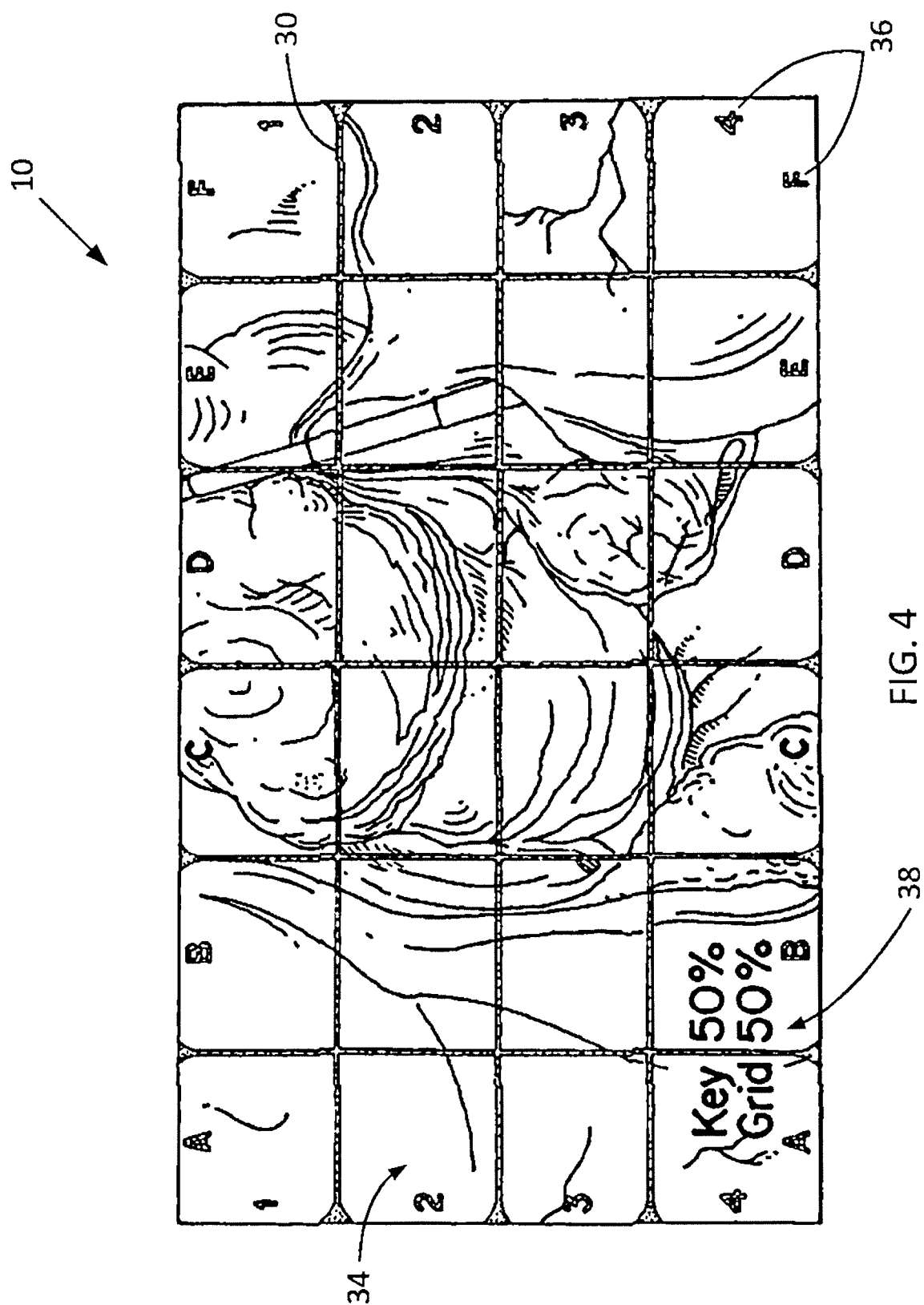

In one example, the overlay pattern 30 and key 36 can be applied to the surgical image in varying levels of opacity. The overlay may also include an indicator 38, which may display certain properties of the overlay 30 as set by the user. For example, FIG. 3 illustrates the overlay 30 as a grid and key 36 applied at 100% opacity. FIG. 4 illustrates the overlay 30 and the key 36 both applied at 50% opacity. The properties of the overlay 30 can be constant or can vary across the display 32. For example, the overlay pattern 30 can be more opaque at the edges of the display 32 and gradually become more transparent toward the center of the display 32.

Figure 5:
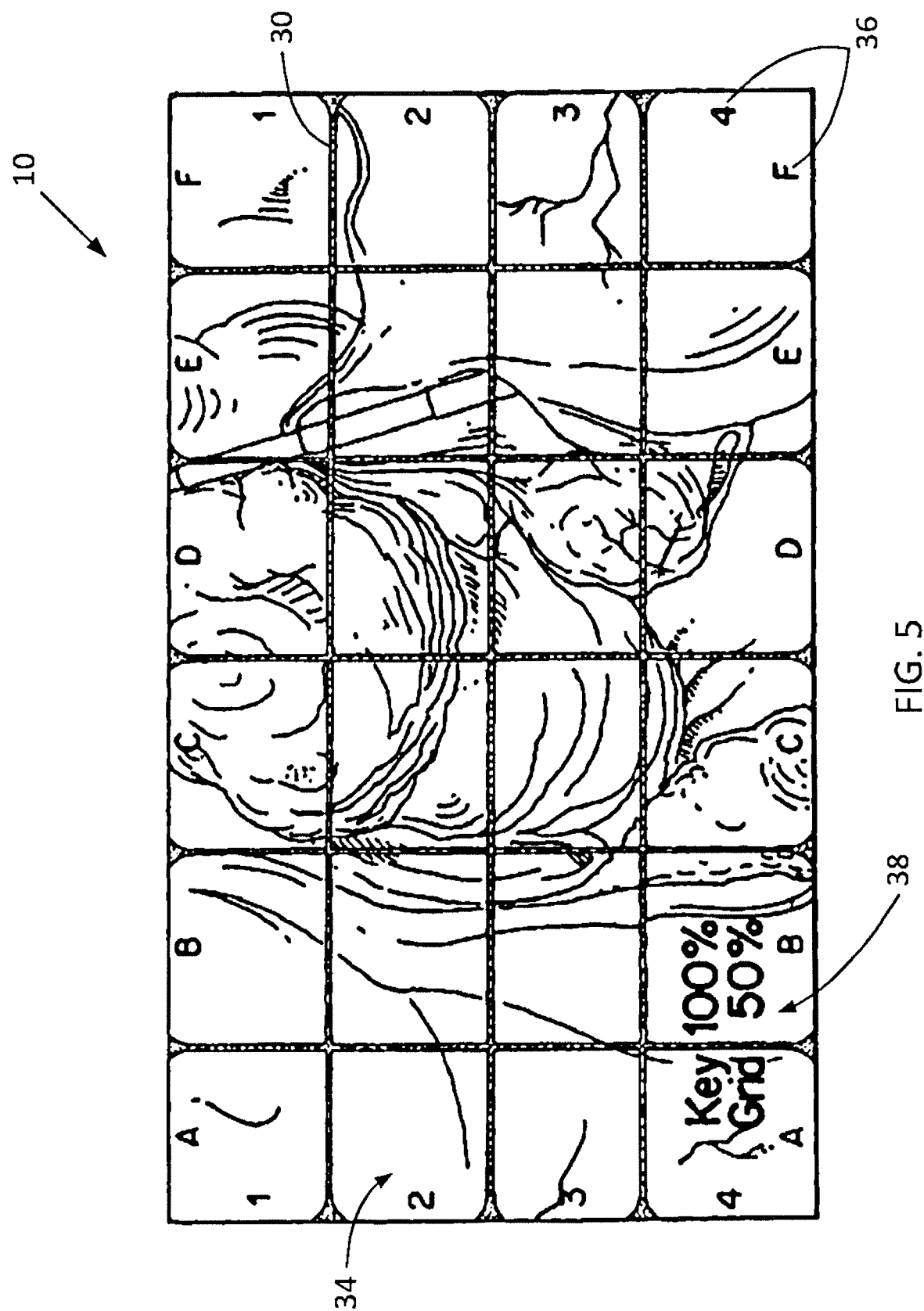

In a further embodiment, the adjustable properties of the overlay pattern and coordinates may be adjusted independently of one another. For example, as shown in FIG. 5, the overlay may be set to 50% opacity whereas the key 36 may be maintained at 100% opacity.

Various properties of the camera control unit (CCU) may also be changed so as to effect a change in the surgical image data 34 at and/or around certain coordinates or a region of the overlay 30 identified by the user. For example, the brightness, contrast, color, or zoom of the surgical image data 34 may be adjusted at and/or around the coordinates or region identified. The coordinates or region of the overlay 30 may be identified via an input 18, for example by button press on the source 12 or by touching an icon or the display window 26 of a touchscreen 20. The system 10 may also be configured to include voice recognition of certain regions or coordinates of the overlay pattern 30 to change the properties of the CCU.

Moreover, the zoom level of the surgical image data 34 itself may be adjusted independent of the overlay pattern 30. The resolution of the overlay pattern 30 will remain the same, while the surgical image data 34 is zoomed in or out.

Figure 6:
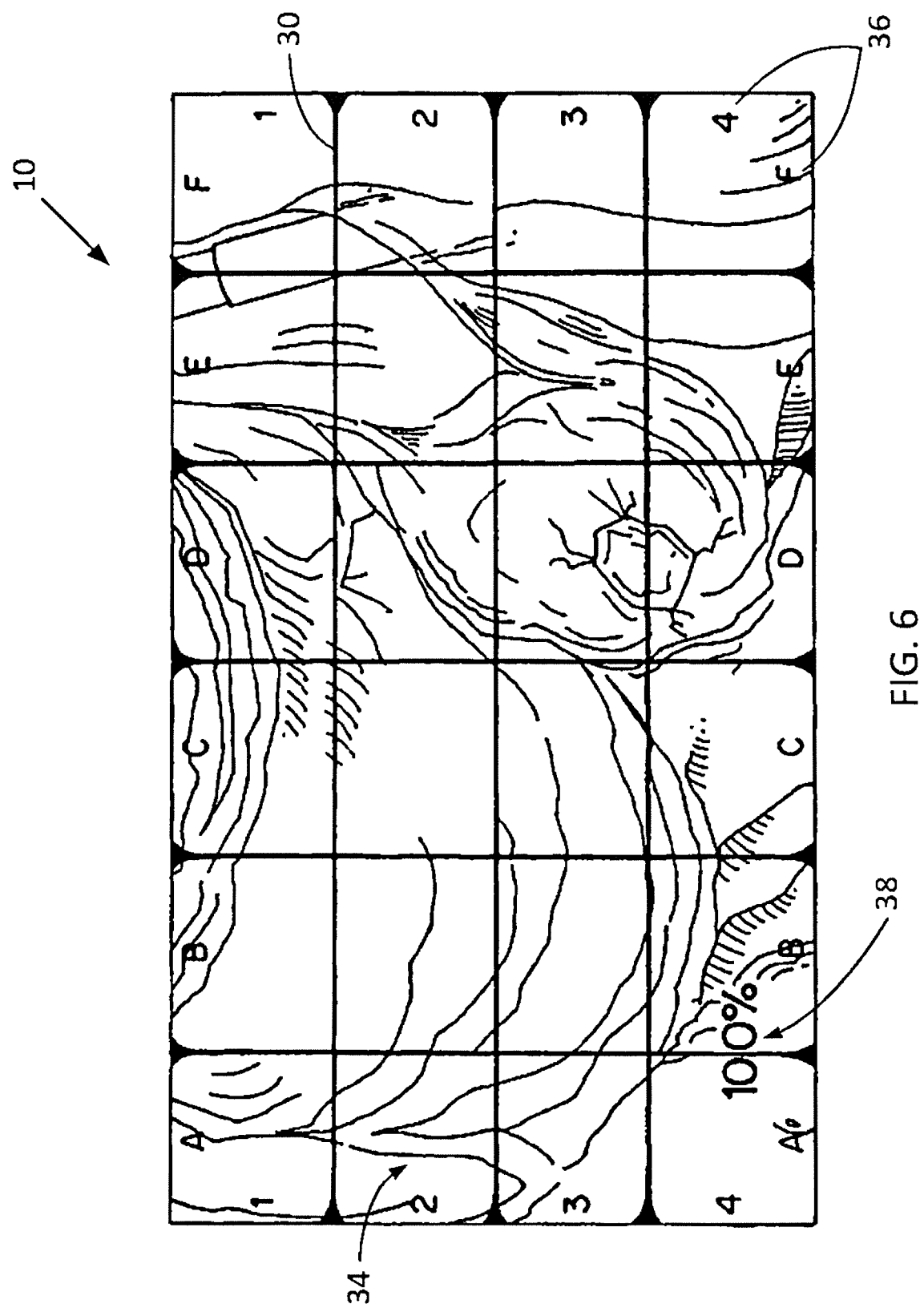
Figure 7:
Figure 8:
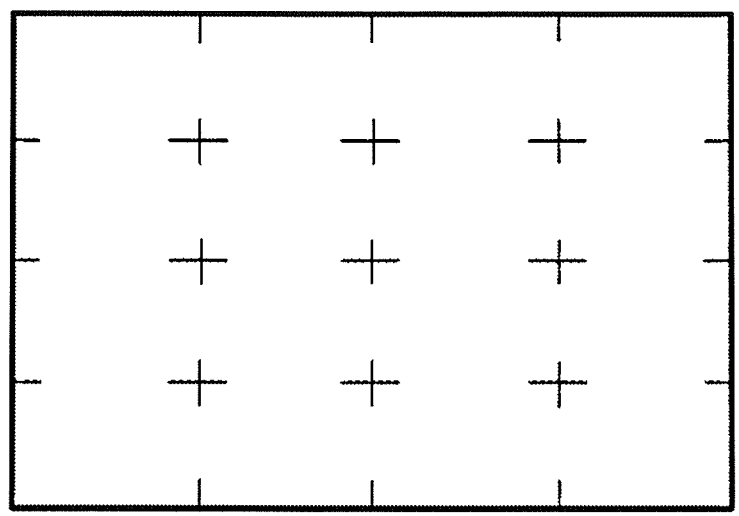
Figure 9:
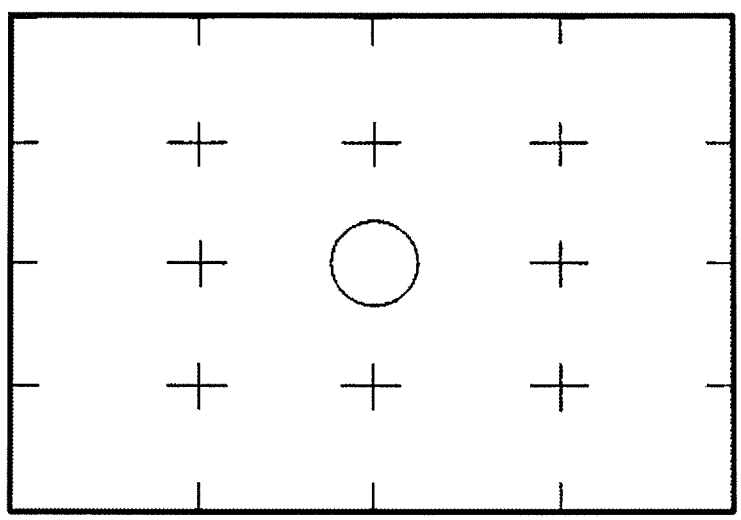
Figure 10:
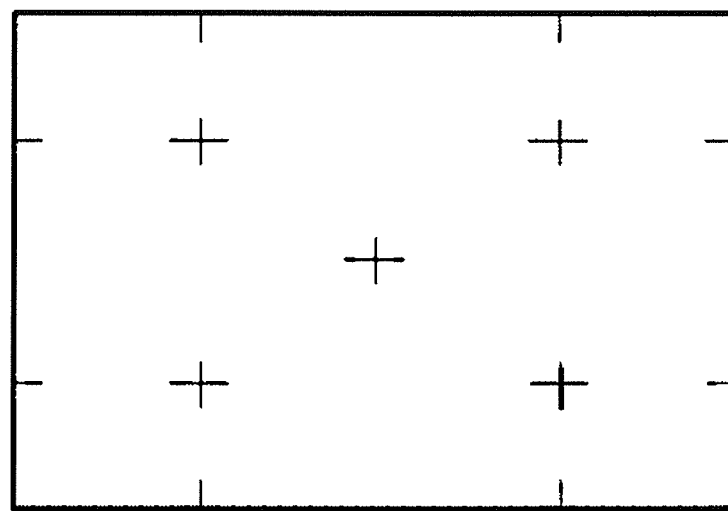

For example, FIG. 6 illustrates a zoomed-in version of the surgical image data 34 of FIG. 3, where the resolution of the grid overlay pattern remains constant (4 rows by 6 columns).

The user may set or adjust the properties of the overlay pattern 30 and/or the key 36 at the beginning of, or during, a surgical procedure. For example, the user may select a grid overlay, choose the number of columns and rows, and set the color all at prior to commencing a surgical procedure. The user may also establish presets to which the overlay 30 will default. In one embodiment shown in FIGS. 1-7, the resolution of the grid overlay is four rows by six columns. However, other grid overlay resolutions are contemplated, such as 4×4. The overlay can be of a varying number or a fixed number of columns, rows, quadrants, etc.

Figure 14:
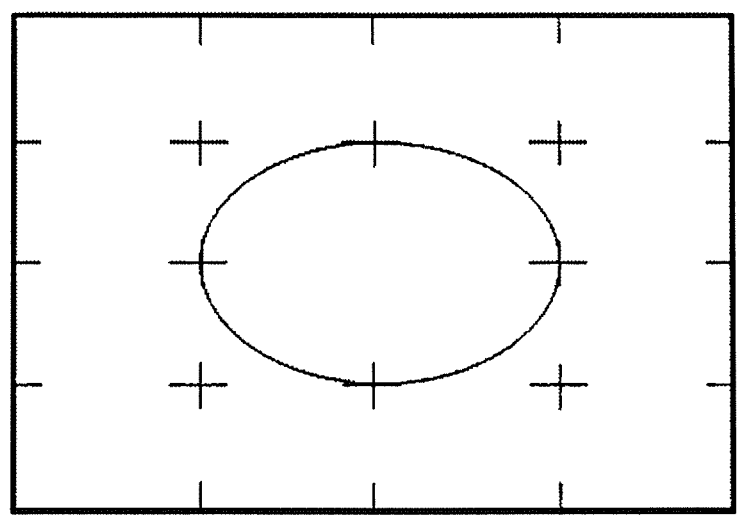
Figure 15:
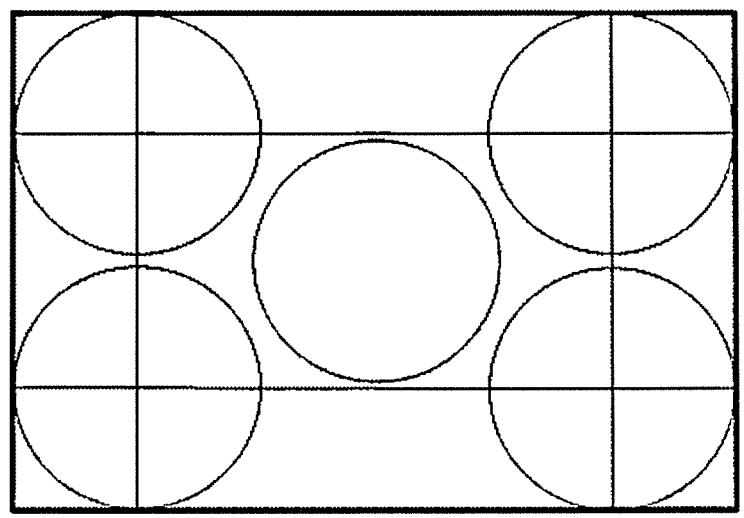

Additionally, the overlay pattern and/or resolution may be preset or chosen by the surgeon in accordance with the aspect ratio of the display monitors. For example, the surgeon may chose a standard definition (SD) display having a 4×3 aspect ratio and the overlay pattern would be chosen or adjusted accordingly. The surgeon may also chose a high definition (HD) display having a 16×9 aspect ratio and the overlay pattern would be chose or adjusted accordingly. Overlay patterns incorporating ovals, such as the pattern shown in FIG. 15, are well suited for HD displays whereas overlay patterns incorporating circles, such as the pattern shown in FIG. 14, are well suited for SD displays.

In a further embodiment, the system 10 may automatically enable the overlay if a motion vector detector (as an input 18) senses a still image for a certain period of time. Conversely, the system 10 may automatically disable the overlay if a motion vector detector senses a moving image for a certain period of time. Further, the system 10 may automatically "time out" after the overlay has been enabled for a preset period of time, or "time-out" if the surgical image has been still for a certain period of time.

When the overlay is enabled or disabled, either by automatic sensing, "time-out" or by direct input from the user, the overlay could be programmed to either immediately appear at 100% opacity or immediately disappear. Alternatively, the overlay could be programmed to gradually appear or disappear by gradual increase or decrease in opacity. These properties will be discussed further below.

Figure 22:
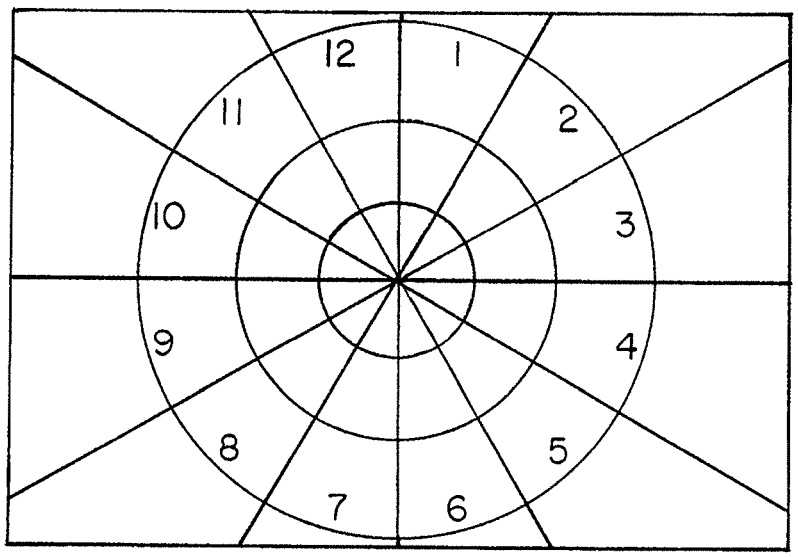
Figure 24:
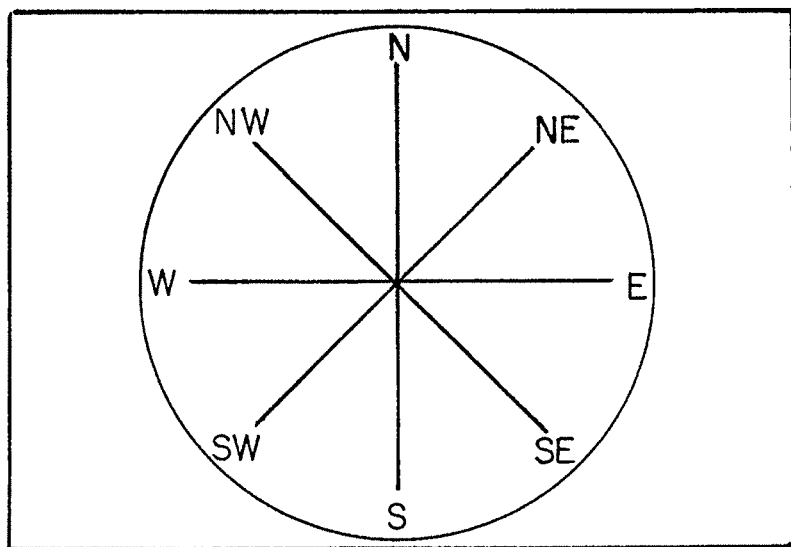
Figure 25:
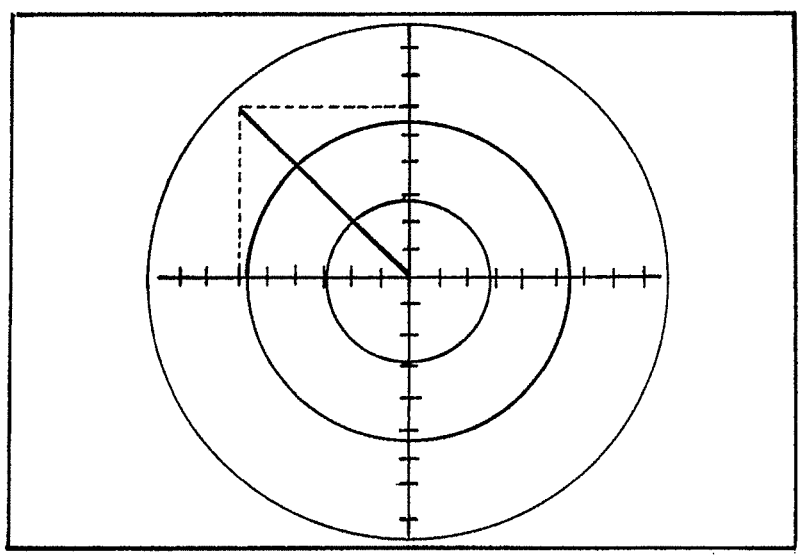

In addition to the overlay pattern recited before, the overlay pattern may include a set of centric lines originating from a single point, such as from the center of the monitor screen, and optionally ending near the edges of the monitor screen, as shown in FIGS. 22, 24 and 25. Preferably, the centric lines are shown for every 15 degrees, 20 degrees, 30 degrees, 45 degrees, 60 degrees, 90 degrees, or other predetermined degrees. When the centric lines are shown for every 30 degrees, the circular overlay pattern is "clock" like. When the centric lines are shown for every 45 degrees, the circular overlay pattern is "compass" like. When the centric lines are shown for every 90 degrees, the circular overlay pattern is a "quadrant" like.

Figure 23:
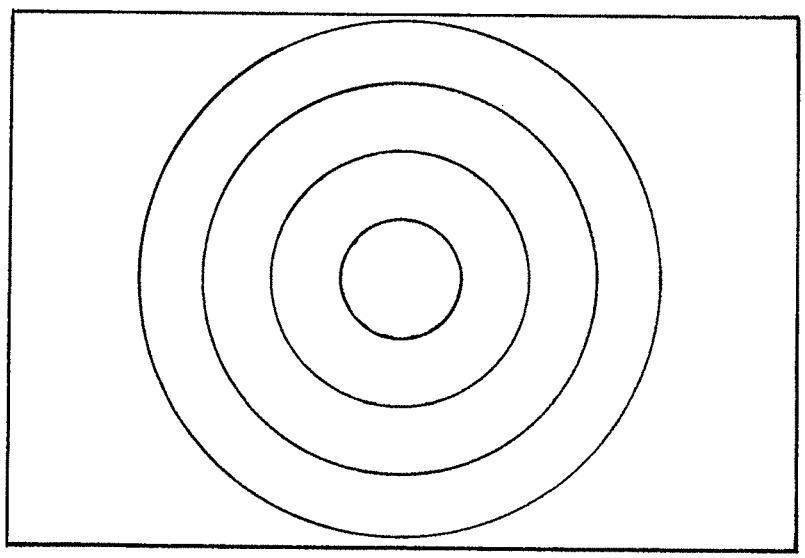

The overlay pattern may include a series of concentric shapes. Preferably, the concentric shapes are concentric circles, concentric ovals, or concentric polygons. More preferably, the concentric shapes are concentric circles (also called centric circles), as shown in FIGS. 22, 23 and 25. In one embodiment, as shown in FIGS. 22 and 25, the overlay pattern contains three concentric circles, at 25%, 50% and 100% of the monitor height.

The overlay pattern may be formed by superimposing the centric lines on the concentric shapes, as shown in FIGS. 22, 24 and 25. In one embodiment, the overlay pattern is formed by a wind rose going from 0 degree to 360 degrees with centric lines at every 20 degree or 30 degrees and two concentric circles at 25% and 50% of the monitor height. Preferably, the single originating point of the centric lines is also the center of the concentric shapes.

As stated before, the overlay pattern may include an optional key 36 for assisting the user in identifying and discussing areas or portions of the overlay pattern 30, and, in turn, identifying and discussing an area of interest on the underlying surgical image data 34.

For the "clock" like overlay pattern as shown in FIG. 22, the centric lines may be labeled as 1, 2, 3, . . . , 12, corresponding to the conventional positions of 1 o'clock, 2 o'clock, 3 o'clock, . . . , 12 o'clock. For the "compass" like overlay pattern, as shown in FIG. 24, the centric lines can be marked as N, NE, E, SE, S, SW, W, and NW, corresponding to a conventional compass. The "quadrant" like overlay pattern, as shown in FIG. 25, may be labeled as x-axis and y-axis, which may in turn be labeled with numbers as conventional coordinates.

The concentric circles can be labeled with an alphanumeric key, or other suitable number and/or letter characters. If there are a total of three concentric circles, they can be referred as inner, medium, and outer circles, or small, middle, and large circles.

The overlay patterns formed by superimposing the centric lines on the concentric circles are particular useful for identifying areas of interest in some circumstances. For instance, the small circle of FIG. 22 is suitable for showing a small circular image, such as an image of 4 mm scope or a magnified laparoscopic image. Thus the small circle of FIG. 22 can be used for identifying the precise targeting area of an image object, leaving the other area of the imaged object outside the small circle. To further highlight the image area within the small circle, the small circle of the concentric circles can be made transparent, while the area outside the small circle gradually becomes opaque.

The designs of concentric shapes, centric lines, concentric shapes superimposed on centric lines, and the previously described designs, such as grid, crosshair, quadrant, hash mark, can be used interchangeably for the overlay pattern 30. Collectively, they form a plurality of designs for the overlay pattern 30.

Figure 1A:
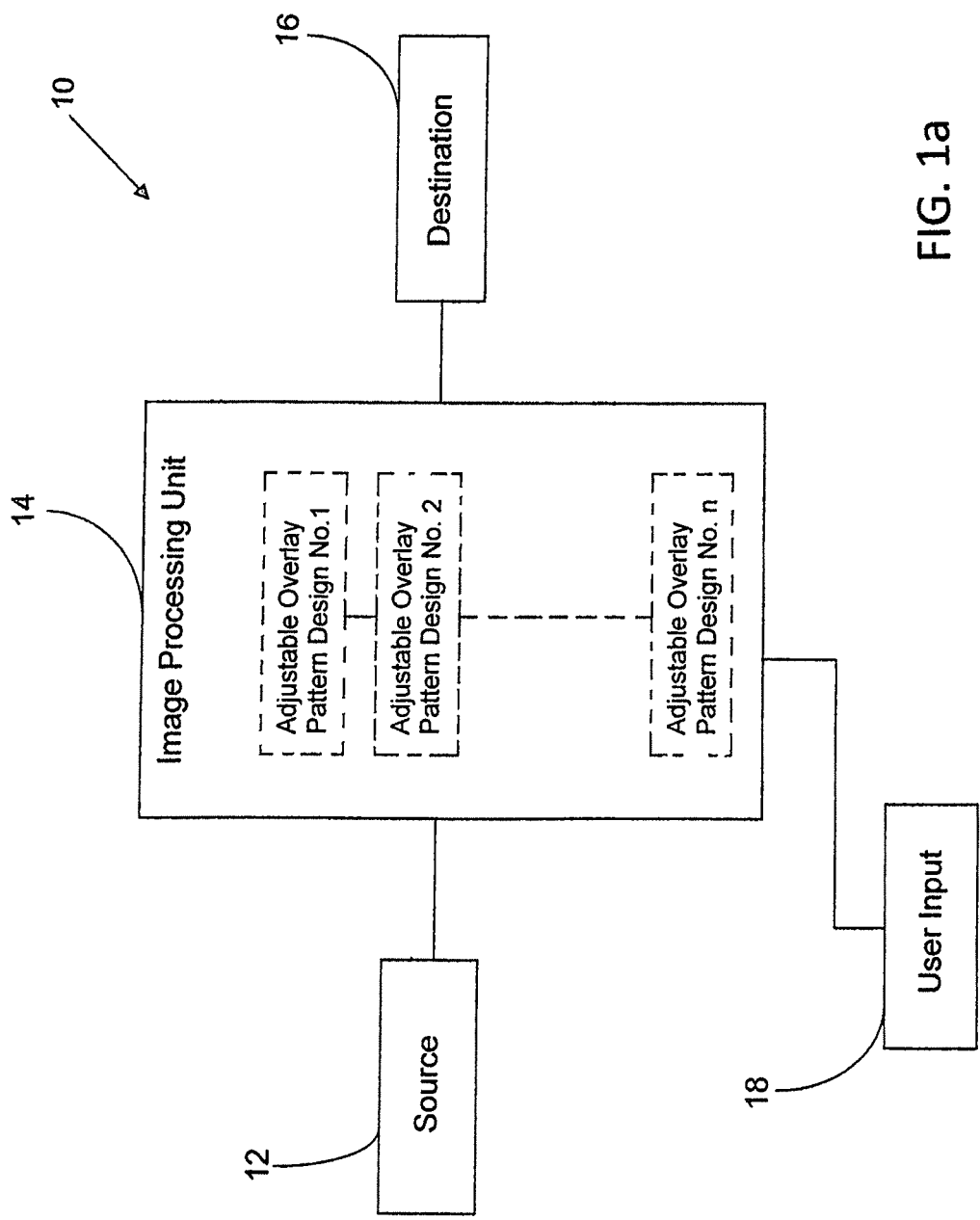
FIG. 1a is a schematic illustration of one embodiment of a system for identifying an area of interest on a surgical image, which includes a plurality of designs for an overlay pattern available in an image process unit.

As illustrated in FIG. 1a, the system 10 in accordance with the present invention includes a source 12, an image processing unit 14, and a destination 16. The source 12 is typically connected with the processing unit 14 by wires or cables to transmit surgical image data 34. However, the source 12 may also wirelessly transmit signals to the processing unit 14. The process unit 14 includes a plurality of designs for the overlay pattern 30 to suit different display needs, and a software executing on the image processing unit for combining the surgical image data 34 from the source 12 with an overlay pattern 30 and further adjusting the properties of the overlay pattern, such as activation, deactivation, resolution, opacity, opacity distribution, color, brightness, thickness, and size. The software can also be designed to select the desired overlay pattern 30 in response to a user input 18. The user input 18 can be provided by a manual command, a voice command, or preset by a user prior to a surgical procedure. For enabling the user input 18 via a voice command, the software is configured with voice recognition features. The plurality of the overlay pattern designs can be numbered for easy identification and selection.

As described above, the zoom level of the surgical image data 34 itself may be adjusted independent of the overlay pattern 30, and the software executing on the image processing unit is designed to enable this feature. Unlike the prior art references that use the overlay as part of a reference for measurement, which usually require the overlay pattern 30 and the surgical image data 34 be zoomed in or out at the same level simultaneously, the present invention uses the overlay pattern as an aid to allow a surgeon or other observers to identify an area of interest, which often requires keeping the overlay pattern 30 constant while zooming in or out of the areas of interest. Since size measurement of an imaged object is not required, the apparatus of the present invention does not include other components usually associated with the size measurement. As a result, the apparatus of the present invention is simple and cost effectiveness for its intended purpose.

By selecting and superimposing the overlay pattern 30 with optional key 36 on a surgical image, the present invention eliminates the need of using a laser pointer, cursor, "circling," or other annotating or marking means by a person to identify areas of interest, as required by the prior art. Thus the present invention provides an effective and clear communication regarding certain areas of interest displayed on the live surgical monitor.

It should be understood that the foregoing is illustrative and not limiting, and that obvious modifications may be made by those skilled in the art without departing from the spirit of the invention.

What is claimed is:

1. A system for identifying an area of interest on a surgical image, comprising:
    a hand-held endoscope coupled to an endoscopic camera, the endoscopic camera supplying a source of surgical image data;
    a camera control unit connected to the endoscopic camera and receiving the surgical image data;
    a plurality of predefined overlay patterns stored on computer readable medium of the camera control unit, the plurality of predefined overlay patterns for identifying an area of interest on the surgical image data;
    an interface receiving user input for selecting a selected overlay pattern from the plurality of predefined overlay patterns, the interface including at least one of a voice module receiving user input in the form of voice commands, and a button on the endoscopic camera;
    the camera control unit processing the surgical image data and combining the selected overlay pattern with the surgical image data;
    at least one destination receiving the surgical image data combined with the selected overlay pattern, the destination including a display displaying the surgical image data combined with the selected overlay pattern;
    the interface receiving user input for configuring a property of the selected overlay pattern when it is displayed on the display in combination with the surgical image data, the property at least one of: contrast, resolution, opacity, opacity distribution, color, brightness, thickness, and size.

2. The system of claim 1, wherein the interface further comprises a touchscreen.

3. The system of claim 1, wherein the selected overlay pattern is selected from the group consisting of concentric circles, concentric ovals, and concentric polygons.

4. The system of claim 3, wherein the selected overlay pattern comprises concentric circles, with diameters of the concentric circles at 25% and 50% of the height of the display.

5. The system of claim 1, wherein the selected overlay pattern comprises centric lines that originate from a single point on the display and are shown for every 15 degrees, 20 degrees, 30 degrees, 45 degrees, 60 degrees, or 90 degrees.

6. The system of claim 1, wherein the selected overlay pattern comprises concentric circles superimposed on a set of centric lines originated from a single point, the single point being the center of the concentric circles.

7. The system of claim 6, wherein the diameters of at least two of the concentric circles are at 25% and 50% of the height of the display.

8. The system of claim 6, wherein the area of interest of the surgical image data is displayed in the smallest circle of the concentric circles.

9. The system of claim 1, wherein the selected overlay pattern includes a key comprising a plurality of alphanumeric characters identifying areas of the selected overlay pattern.

10. The system of claim 1, wherein the display presents the surgical image data or the surgical image data in combination with the selected overlay pattern as a picture-in-picture.

11. The system of claim 1, wherein the selected overlay pattern is enabled or disabled in response to data input from a motion vector detector detecting movement in the surgical image data.

12. The system of claim 1, wherein the selected overlay pattern is enabled or disabled in response to data input from an accelerometer sensing movement of the endoscope.

13. The system of claim 1, wherein the user input is provided by a button on the endoscopic camera.

14. The system of claim 1, wherein the user input is provided by selection of an icon on a touch screen, the icon corresponding to the selected overlay pattern.

15. The system of claim 1, wherein the user input is provided by a voice command by a user.

16. The system of claim 1, wherein the destination comprises a recording device storing the surgical image data combined with the selected overlay pattern.

* * * * *